US012575720B2

(12) United States Patent
Ralph et al.

(10) Patent No.: US 12,575,720 B2
(45) Date of Patent: Mar. 17, 2026

(54) REAL-TIME SAMPLING DEVICE

(71) Applicant: Olympus Medical Systems Corporation, Hachioji (JP)

(72) Inventors: Christopher Ralph, Seattle, WA (US); Jean-Martin Baillargeon, Seattle, WA (US); David A. Herrin, Seattle, WA (US)

(73) Assignee: Olympus Medical Systems Corporation, Tokyo (JP)

( * ) Notice: Subject to any disclaimer, the term of this patent is extended or adjusted under 35 U.S.C. 154(b) by 947 days.

(21) Appl. No.: 17/554,254

(22) Filed: Dec. 17, 2021

(65) Prior Publication Data

US 2022/0257095 A1 Aug. 18, 2022

Related U.S. Application Data

(60) Provisional application No. 63/150,708, filed on Feb. 18, 2021.

(51) Int. Cl.
*A61B 1/00* (2006.01)
*B01L 3/00* (2006.01)

(52) U.S. Cl.
CPC .......... *A61B 1/00147* (2013.01); *B01L 3/508* (2013.01); *B01L 2300/042* (2013.01); *B01L 2300/0609* (2013.01); *B01L 2300/123* (2013.01)

(58) Field of Classification Search
CPC . A61B 1/00147; A61B 1/0128; A61B 1/0011; A61B 1/00098; A61B 1/00087;

(Continued)

(56) References Cited

U.S. PATENT DOCUMENTS 10,507,270 B1 12/2019 Sabin et al.
11,116,385 B2 * 9/2021 Hosogoe ............ G02B 23/2423
(Continued)

FOREIGN PATENT DOCUMENTS

CN 205234537 5/2016
CN 107106021 8/2017
(Continued)

OTHER PUBLICATIONS

"United Kingdom Application Serial No. 2202169.5, First Examination Report Under Section 18(3) mailed Oct. 25, 2024", 3 pgs.
(Continued)

*Primary Examiner* — Alex M Valvis
*Assistant Examiner* — Jonathan M Haney
(74) *Attorney, Agent, or Firm* — Schwegman Lundberg & Woessner, P.A.

(57) ABSTRACT

Various disclosed embodiments include illustrative apparatuses and systems for performing multi-lumen catheter functions and methods for making the apparatuses. An illustrative apparatus includes a multi-lumen sheath, a cap having a proximal end attachable to a distal end of the multi-lumen sheath, and a liner. The cap includes a ramp section having a ramp and an exit port and an imaging section disposed distally from the ramp section. The ramp allows travel of a medical device from within the liner to the exit port. The distal ramp section extends distally from the flexible proximal section and is received by the ramp of the ramp section. The distal ramp section has a curved portion. The cap includes a socket for receiving a tab of the distal ramp section. The curved portion includes bending relief features.

20 Claims, 8 Drawing Sheets

(58) Field of Classification Search
CPC . A61B 1/018; A61B 1/00137; A61B 1/00101; A61B 1/0623; A61B 1/00131; A61B 8/12; A61B 10/02; A61B 10/04; A61B 10/06; A61B 10/0275; A61B 2010/0225; B01L 3/508; B01L 2300/042; B01L 2300/0609; B01L 2300/123; G02B 23/24
See application file for complete search history.

(56) References Cited

U.S. PATENT DOCUMENTS

| | | | |
|---|---|---|---|
| 2007/0244353 | A1 | 10/2007 | Larsen |
| 2007/0265548 | A1* | 11/2007 | Goldenberg ......... A61B 10/025 600/567 |
| 2008/0188890 | A1* | 8/2008 | Weitzner ............ A61B 1/00165 606/205 |
| 2010/0087705 | A1* | 4/2010 | Byers .................... A61M 39/06 600/104 |
| 2015/0173592 | A1* | 6/2015 | Leeflang .......... A61B 17/00234 |
| 2016/0317154 | A1* | 11/2016 | Kimura ............ A61B 17/32056 |
| 2019/0059702 | A1 | 2/2019 | Hosogoe |
| 2019/0090862 | A1 | 3/2019 | O'callaghan et al. |
| 2019/0231173 | A1 | 8/2019 | Hosogoe |
| 2019/0247029 | A1* | 8/2019 | Field ................ A61B 17/32053 |

FOREIGN PATENT DOCUMENTS

| | | |
|---|---|---|
| CN | 114947993 A | 8/2022 |
| DE | 102022103556 A1 | 8/2022 |
| EP | 3158913 A1 | 4/2017 |
| EP | 3165171 A2 | 5/2017 |
| GB | 2605694 A | 10/2022 |
| GB | 2605694 B | 5/2025 |
| JP | 2007215634 | 8/2007 |
| JP | 2007252458 | 10/2007 |
| JP | 2011206428 | 10/2011 |
| JP | 2012070792 | 4/2012 |
| JP | 2013176559 | 9/2013 |
| JP | 2022126612 | 8/2022 |

OTHER PUBLICATIONS

"United Kingdom Application Serial No. 2202169.5, Response filed Dec. 20, 2024 to First Examination Report Under Section 18(3) mailed Oct. 25, 2024", w claims, 17 pgs.

"France Application Serial No. 2201422, Office Action mailed May 6, 2022", with machine translation, 8 pgs.

"France Application Serial No. 2201422, Response filed Jul. 5, 2022 to Office Action mailed May 6, 2022", w/ English claims, 49 pgs.

"United Kingdom Application Serial No. 22021695, Search Report mailed Jul. 20, 2022", 3 pgs.

"Chinese Application Serial No. 202210151304.2, Office Action mailed Mar. 5, 2025", w/ English translation, 15 pgs.

"Chinese Application Serial No. 202210151304.2, Response filed Jun. 10, 2025 to Office Action mailed Mar. 5, 2025", w/ english claims, 10 pgs.

"Chinese Application No. 202210151304.2, Response to Examiner Telephone Interview filed Oct. 17, 2025", w claims, 8 pgs.

"Japanese Application Serial No. 2022-022830, Notification of Reasons for Rejection mailed Oct. 28, 2025", W English Translation, 10 pgs.

* cited by examiner

REAL-TIME SAMPLING DEVICE

PRIORITY CLAIM

This application claims the benefit of U.S. Provisional Application Ser. No. 63/150,708, filed Feb. 18, 2021, the contents of which are hereby incorporated by reference.

BACKGROUND

The statements in this section merely provide background information related to the present disclosure and may not constitute prior art.

Inserting and manipulating thin, elongated instruments within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Correspondingly, elongated instruments also may be used to collect samples from within a body in a relatively noninvasive matter. For example, when a biopsy from a lung is needed to determine whether a detected lesion is cancerous, instead of cutting into the patient's chest to procure a sample, an insertion device such as a bronchoscope may be used to guide one or more elongated instruments to a location near the lesion to procure a sample. However, merely conveying the elongated instruments to the location near the lesion may present only a part of what is needed to sample the lesion itself.

BRIEF SUMMARY

Various disclosed embodiments include illustrative apparatus and systems for taking tissue samples.

In an illustrative embodiment, an apparatus includes a multi-lumen sheath, a cap having a proximal end attachable to a distal end of the multi-lumen sheath, and a liner. The cap includes a ramp section having a ramp and an exit port and an imaging section disposed distally from the ramp section. The ramp allows travel of a medical device from within the liner to the exit port. The liner includes a flexible proximal section and a distal ramp section having a C-shaped cross-section. The distal ramp section extends distally from the flexible proximal section and is received by the ramp of the ramp section of the cap. The distal ramp section includes a longitudinal axis having a radius of curvature along at least a portion of the distal ramp section.

In another illustrative embodiment, the cap includes a socket disposed at a distal end of the ramp. The liner further includes a tab disposed distally from the distal ramp section. The tab is received within the socket during assembly. The liner further includes a neck section disposed between the distal ramp section and the tab.

In another illustrative embodiment, a system includes a medical device and a multi-lumen device. The multi-lumen device includes a multi-lumen sheath, a cap having a proximal end attachable to a distal end of the multi-lumen sheath, and a liner. The cap includes a ramp section having a ramp and an exit port and an imaging section disposed distally from the ramp section. The ramp allows travel of the medical device from within the liner to the exit port. The liner includes a flexible proximal section and a distal ramp section having a C-shaped cross-section. The distal ramp section extends distally from the flexible proximal section and is received by the ramp of the ramp section of the cap. The distal ramp section includes a longitudinal axis having a radius of curvature along at least a portion of the distal ramp section.

In another illustrative embodiment, a process is provided for creating apparatus described above.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Illustrative embodiments are illustrated in referenced figures of the drawings. It is intended that the embodiments and figures disclosed herein are to be considered illustrative rather than restrictive.

Like reference symbols in the various drawings generally indicate like elements.

DETAILED DESCRIPTION

The following description explains, by way of illustration only and not of limitation, various embodiments of apparatuses and systems for sampling tissue using a multi-lumen apparatus insertable into a body.

It will be appreciated that various embodiments of the system described herein may aid in the process of deploying and controlling an elongated instrument. In various embodiments, the system includes a multi-lumen apparatus that may include a sheath that encompasses an imaging probe and a sampling needle. The sheath is insertable into a body to reach a targeted tissue to be sampled. The imaging probe may be used to locate the tissue or a portion of the tissue of interest to be sampled. The sampling needle may be used to procure a sample of that tissue.

In various embodiments, the system may be coupled with an insertion device, such as an endoscope or a bronchoscope, that includes an insertion conduit insertable into a body via an orifice or other opening. The insertion device enables the insertion conduit to be inserted into the body and directed to a desired location within the body. The insertion conduit may be configured to receive the multi-lumen apparatus that is extendable through the insertion conduit. The multi-lumen apparatus is insertable into the body via the insertion device to procure a tissue sample at the desired location within the body. An illustrative multi-lumen apparatus is described below.

Figure 1:
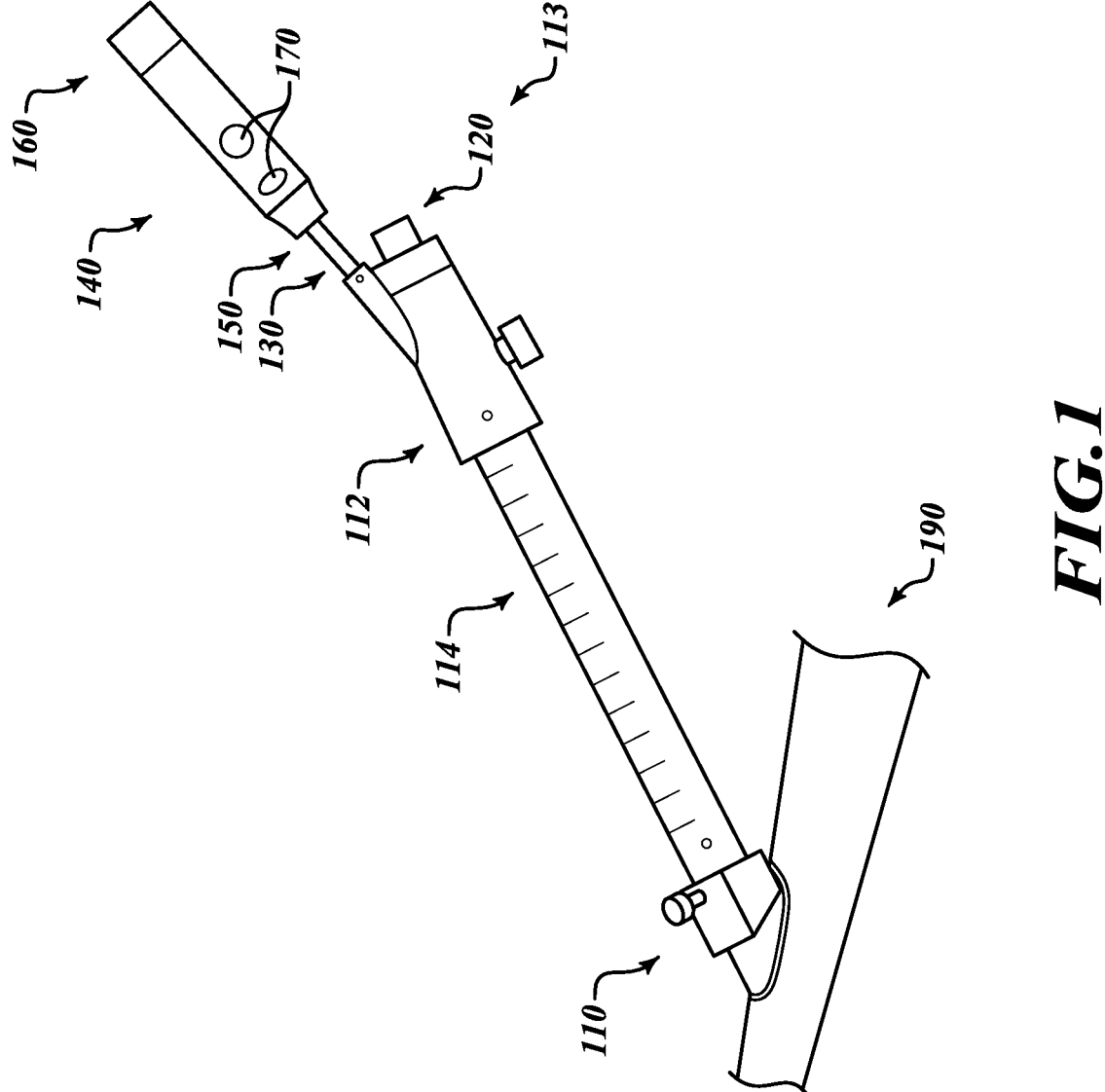
FIG. 1 is a side view of an illustrative sampling system.

In various embodiments, as shown in FIG. 1 an illustrative system 12 includes an insertion device 18 (of which only a portion is shown in FIG. 1), such as an endoscope or a bronchoscope. As previously described, the insertion device 18 includes an insertion conduit that is insertable into a body via an orifice or other opening (none of which are shown in FIG. 1). The insertion device 18 receives a multi-lumen catheter device 14 that receives a medical device 16 that may be extended through a lumen of the multi-lumen catheter device 14 to a desired location. As also previously mentioned, in various embodiments, the medical device 16 may include an imaging probe and/or a sampling needle connected to a handle and contained within a sheath (none of which is individually shown in FIG. 1). The medical device 16 is insertable via the multi-lumen catheter device 14 and the insertion device 18 to procure a tissue sample at a desired location within a body.

It will be appreciated that the insertion device 18 may be any of a number of different types of scopes used in medical procedures. The scope may include multi-use or single-use endoscopes, such as bronchoscopes, laparoscope, laryngoscope, etc. The multi-lumen catheter device 14 may be any device that includes two or more lumens located within an insertion tube attached to a handle device. The lumen of the multi-lumen catheter device 14 may be suitable for receiving imaging devices and the medical devices 16. The received imaging devices may include cameras or ultrasound devices, such as a radial ultrasound probe or comparable device. In various embodiments, the multi-catheter device 14 may include a base section rotatably coupled to the insertion device 18 and a port slidably received by the base section. An illustrative multi-catheter system is shown and described in U.S. Provisional Patent Application No. 63/123,731, filed Dec. 10, 2020, the contents of which are hereby incorporated by reference.

In various embodiments, the insertion tube of the multi-lumen catheter device 14 is received within a working channel port of the insertion device 18. The multi-lumen catheter device 14 may be attached to the working channel port. The medical device 16 may include a flexible sheath attached to a first portion of a handle and an operational tool received within the flexible sheath and attached to an actuator portion of the handle. The operational tool may include a tissue aspiration device, such as a flexible needle, a cytology brush or a comparable device. The operational tool may include a lumen that is in communication with a corresponding lumen within the first portion of the actuator portion of the handle.

Figure 2:
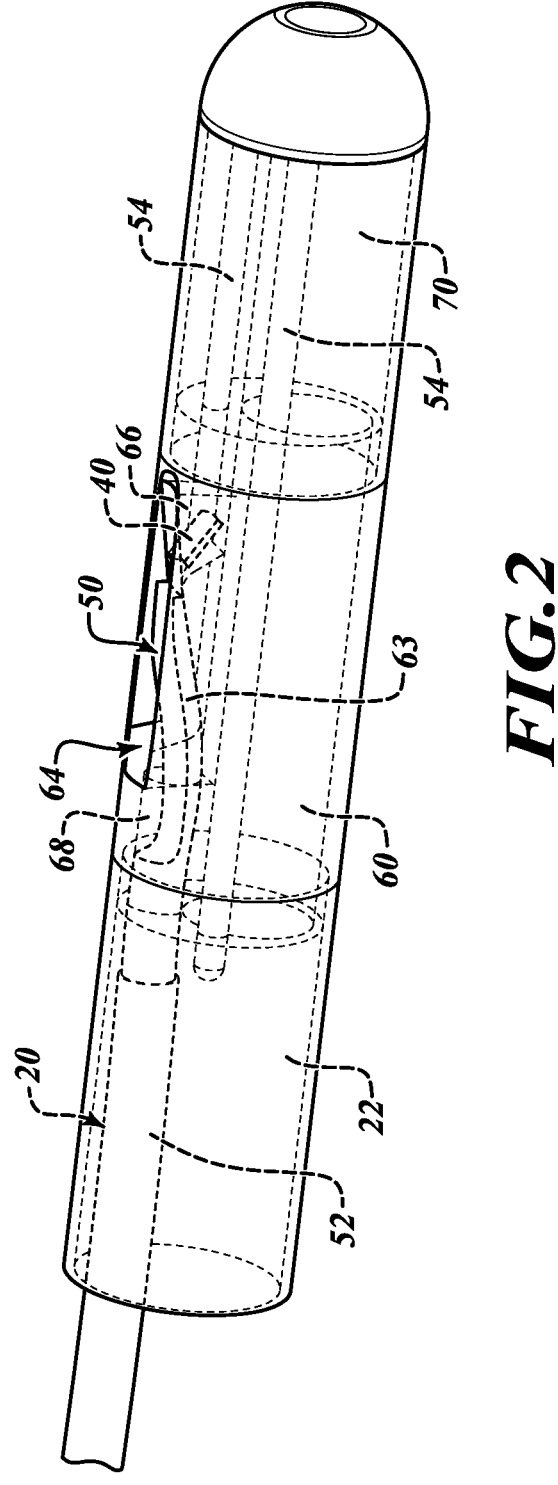
FIG. 2 is an x-ray view of a distal end of a portion of an illustrative multi-lumen catheter used in the system of FIG. 1.

Referring additionally, as shown in FIG. 2, the multi-lumen catheter device 14 includes a flexible multi-lumen sheath having a lumen liner 20 that includes a proximal portion 52 that is attached to a handle (not shown) of the multi-lumen catheter device 14 at a proximal end and a distal ramp section 50 that extends distally from the distal end of the proximal portion 52. The distal ramp section 50 and a small portion of the proximal portion 52 adjacent to the distal ramp section 50 are received within a cap section 60.

The cap section 60 includes a proximal ramp section 62 and a distal cap section 70. A proximal end of the proximal ramp section 62 is attached to a multi-lumen sheath. The multi-lumen sheath 22 receives the lumen liner 20 and extends from the handle of the multi-lumen catheter device 14. The proximal ramp section 62 includes a first lumen 68 that has a proximal end that matches location with a lumen of the multi-lumen sheath 22 when attached thereto. The first lumen 68 includes a ramp 63 that connects the proximal end of the first lumen 68 to an exit port 64 of the proximal ramp section 62 of the cap section 60. The first lumen 68 will be described in more detail below. The distal cap section 70 includes two orientation pins 54 that extend into the proximal ramp section 62.

The proximal ramp section 62 also includes a second lumen for allowing an imaging device to pass from the handle through the multi-lumen sheath 22 to the distal cap section 70.

The proximal ramp section 62 includes a plug cavity 66 located distal from the ramp 63 of the first lumen 68. A distal end of the distal ramp section 50 of the lumen liner 20 includes a bendable tab 40. After the distal ramp section 50 is inserted into the proximal ramp section 62 of the cap section 60, the tab 40 is bent into the plug cavity 66. The tab 40 may be sized to apply a friction force to walls of the plug cavity 66. A medical grade adhesive may be inserted into the plug cavity 66 after the tab 40 is bent therein.

Figure 3:
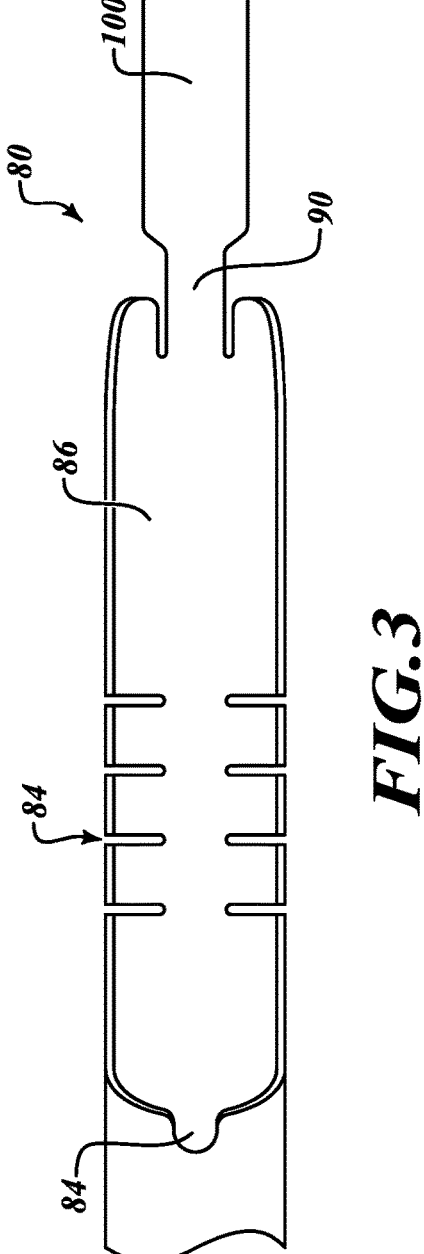
FIG. 3 is a plan view of a component of the system of FIG. 1.
Figure 4:
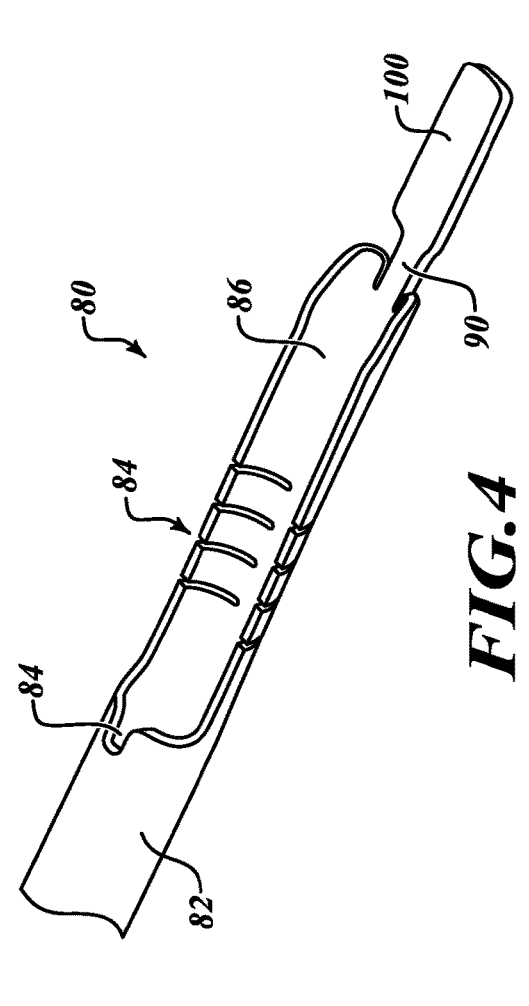
FIG. 4 an isometric view of the component of FIG. 3.

In various embodiments, as shown in FIGS. 3 and 4, an illustrative lumen liner includes a distal ramp section 80 attached to a proximal section 82. The distal ramp section 80 and the proximal section 82 may be formed of a medical grade metal, such as stainless steel, nitinol or a comparable material. The proximal section 82 may be tubular in shape and may include reliefs (not shown) configured to improve flexibility. The distal ramp section 80 is trough-shaped. The distal ramp section 80 includes a curvable section 84 and a straight ramp section 86. The curvable section 84 includes curve relief features, such as laser or machined cuts, for allowing the distal ramp section 80 to curve at the location of the curvable section 84. The number of curve relief features and the type of curve relief features used at the curvable section 84 are selected from any number of variations for producing a desired flexibility and radius of curvature.

The straight ramp section 86 extends distally from the curvable section 84. A distal end of the straight ramp section 86 includes a tab 100 that connects via a neck section 90. The neck section 90 may be partially defined by slits cut longitudinally into the distal end of the straight ramp section 86. The shape and length of the neck section 90 are selected to allow a manufacturer to easily bend the tab 100 into a plug cavity, such as the plug cavity 66 shown in FIG. 2.

In various embodiments, a top edge of the distal end of the proximal section 82 includes a relief cutout 106. The relief cutout 106 is designed to reduce friction with medical devices as they pass back and forth through the proximal section 82 and deflect along the curvable section 84 before passing through an exit port.

Figure 5:
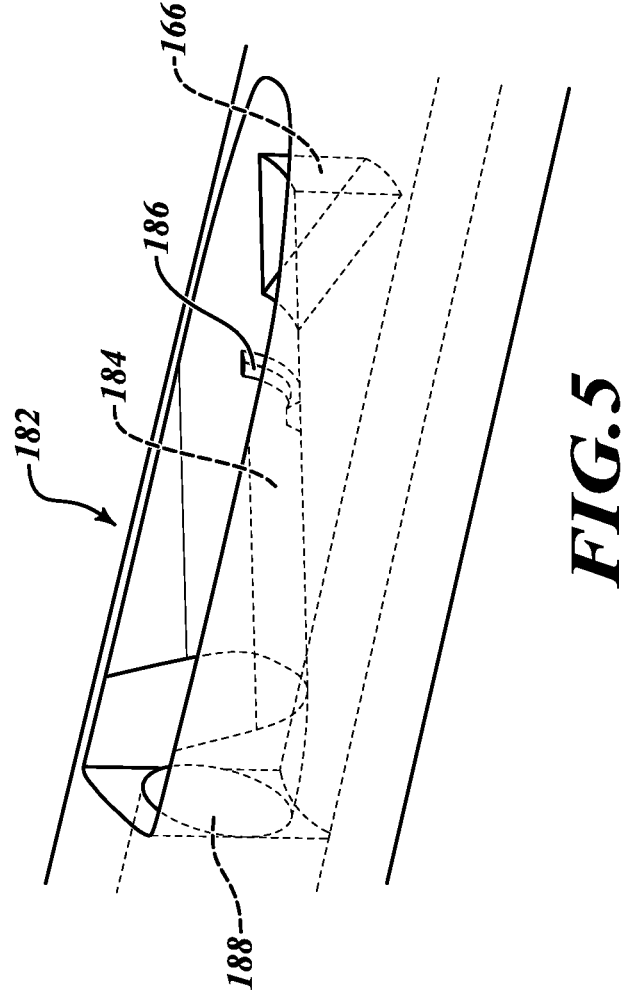
FIG. 5 is a partial x-ray isometric view of a portion of a distal end of a distal tip used in the system of FIG. 1.
Figure 6:
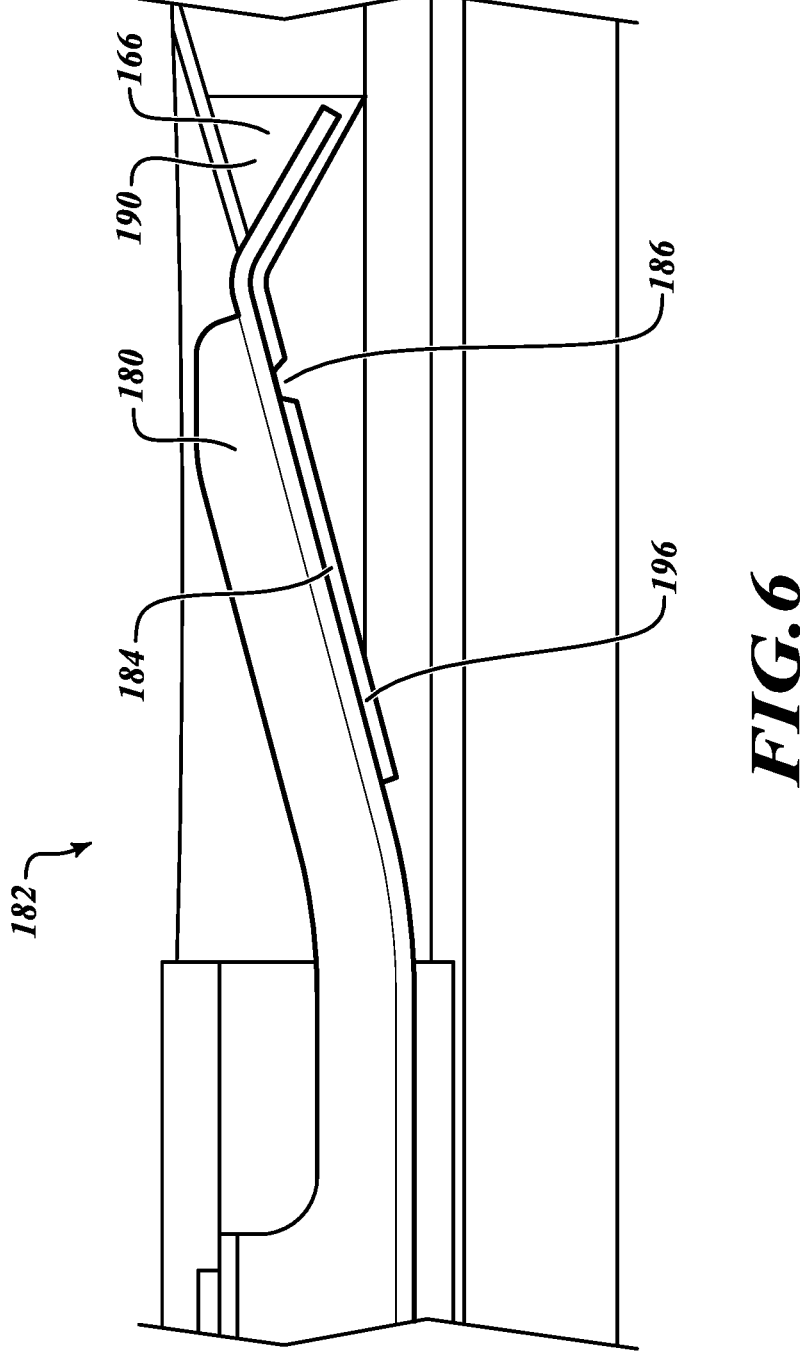
FIG. 6 is a partial x-ray side view of a portion of a distal end of the illustrative multi-lumen catheter and the distal tip used in the system of FIG. 1.

In various embodiments, as shown in FIGS. 5 and 6 a ramp section 182 of a distal cap section for a multi-lumen catheter device is molded or shaped to include a ramp 184 that extends from near a proximal opening 188 of a lumen of the cap section. The ramp 184 includes an adhesive relief 186 that is positioned along the top surface of the ramp 184 closer to a distal end of the ramp 184 than a proximal end. A plug cavity 166 is located distally from a distal end of the ramp 184. The ramp 184 and the plug cavity 166 are exposed to the environment surrounding the ramp section 182 via an exit port.

In various embodiments, before a distal end of a lumen liner 180 is inserted into the ramp section 182, the distal end of a lumen liner 180 may be pre-bent to a desired angle in order to conform with the ramp 184. Also, before the distal end of the lumen liner 180 is inserted into the ramp section 182, an adhesive 196 may be applied to the ramp 184 on either side of the adhesive relief 186. The adhesive relief 186 allows for space between the ramp and the lumen liner 180 for a layer of adhesive 196. If the lumen liner 180 is straight during insertion into the ramp section 182, then the curve relief features, such as those shown and described above in FIGS. 3 and 4, allow the lumen liner 180 to curve according to the angle of the ramp 184. If the adhesive relief 186 and the adhesive 196 are present, then a bond is formed between the ramp 184 and the distal end of the lumen liner 180.

Once the lumen liner 180 is properly positioned within the ramp section 182, then a distal tab 194 attached to the distal end of the lumen liner 180 is mechanically bent into the plug cavity 166. The plug cavity 166 is then filled with adhesive to form an adhesive plug 190, thus holding the tab 194 securely within the plug cavity 166.

Figure 7:
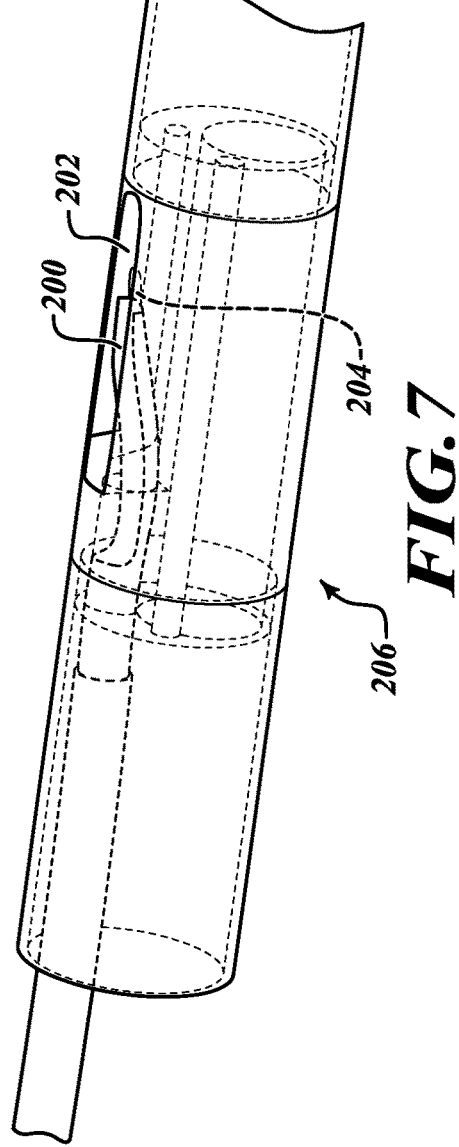
FIG. 7 is a partial x-ray view of isometric a portion of a distal end of an illustrative multi-lumen catheter.

In various embodiments, as shown in FIG. 7 a ramp section 206 of a cap section 208 for a multi-lumen catheter device includes a ramp 202 that bonds to the distal end of a lumen liner 200. The ramp 202 includes a deeper groove section 204 located along a portion of the ramp 202. The deeper groove section 204 is used to receive adhesive prior to insertion of the distal end of the lumen liner 200.

Figure 8:
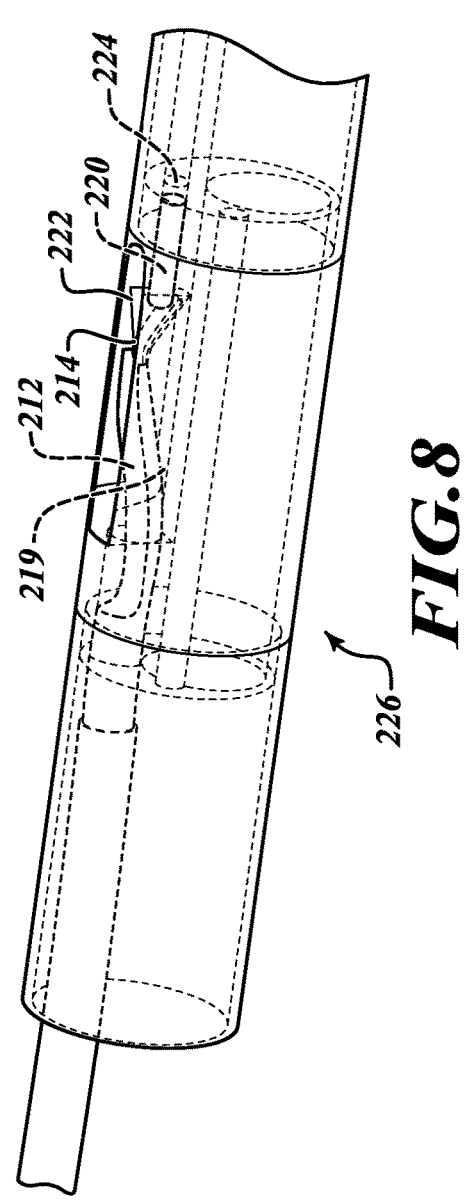
FIG. 8 is a partial x-ray isometric view of a portion of a distal end of an illustrative multi-lumen catheter.

In various embodiments, as shown in FIG. 8 a ramp section 226 of a cap section 218 for a multi-lumen catheter device includes a ramp 219, a plug cavity 222 located distally from the ramp 219, a pin lumen 224, and a locking pin 220. The pin lumen 224 connects between a distal face of the ramp section 226 and a distal wall within the plug cavity 222. After a lumen liner 212 with a distal tab 214 are inserted into the ramp section 226, the tab 214 is mechanically bent into the plug cavity 222 similar to the other tabs described above. After the bending of the tab 214, the locking pin 220 is inserted into the pin lumen 224 such that a proximal end of the locking pin 220 protrudes into the plug cavity 222. The locking pin 220 provide a locking mechanism for the tab 214. At this point, an adhesive may be inserted into the plug cavity 222 around the tab 214 and the locking pin 220.

Figure 9:
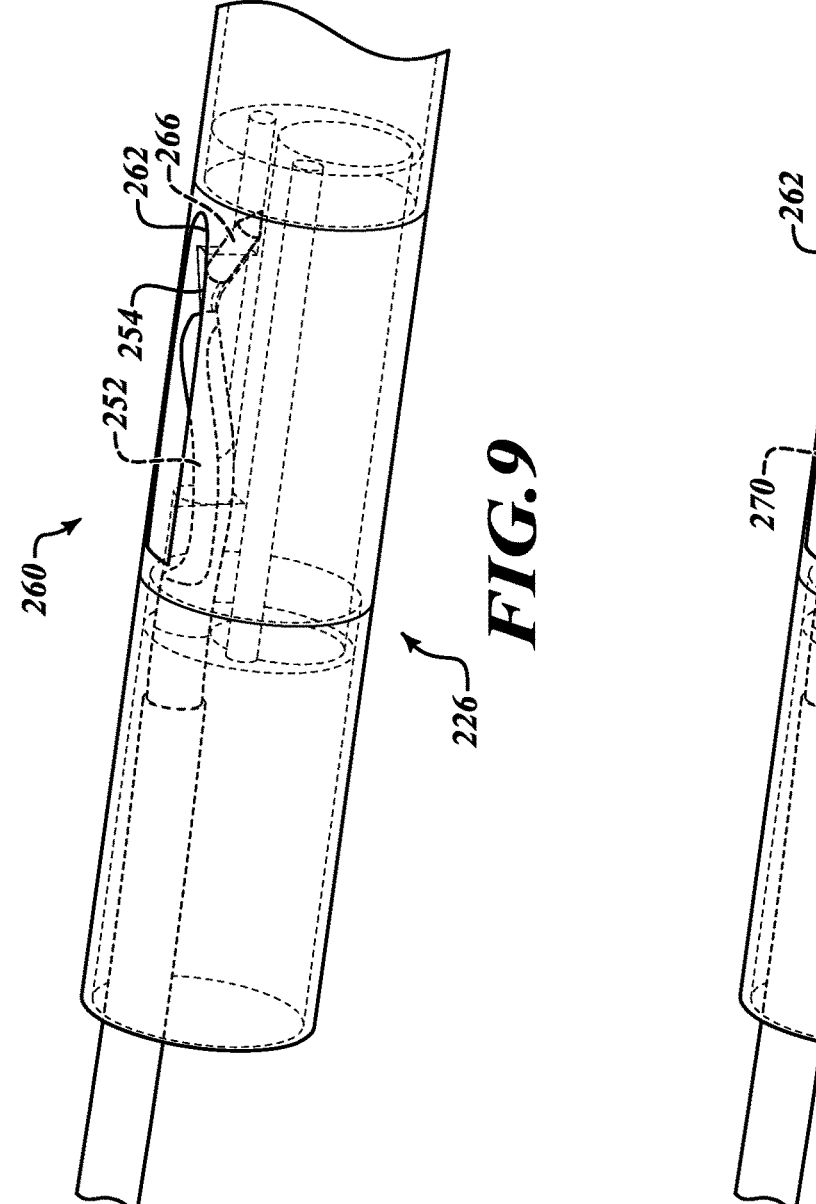
FIG. 9 is a partial x-ray isometric view of a portion of a distal end of an illustrative multi-lumen catheter.

In various embodiments, as shown in FIG. 9 a ramp section 264 of a cap section 260 of a multi-lumen catheter device includes a ramp and a plug cavity 262 for receiving a distal end of the lumen liner 252 and an associated distal tab 254. After the tab 254 is bent into the plug cavity 262, a pin 266 is inserted into the plug cavity 262. The pin 266 includes a pointed distal end. Thus, when the pin 266 is inserted with force into the plug cavity 262, the pointed distal end may embed partially or fully within a distal wall of the plug cavity 262. The pin 266 provides a locking mechanism for the tab 254. After the pin 266 has been inserted, an adhesive may be inserted into the plug cavity 262 around the tab 254 and the pin 266.

Figure 10:
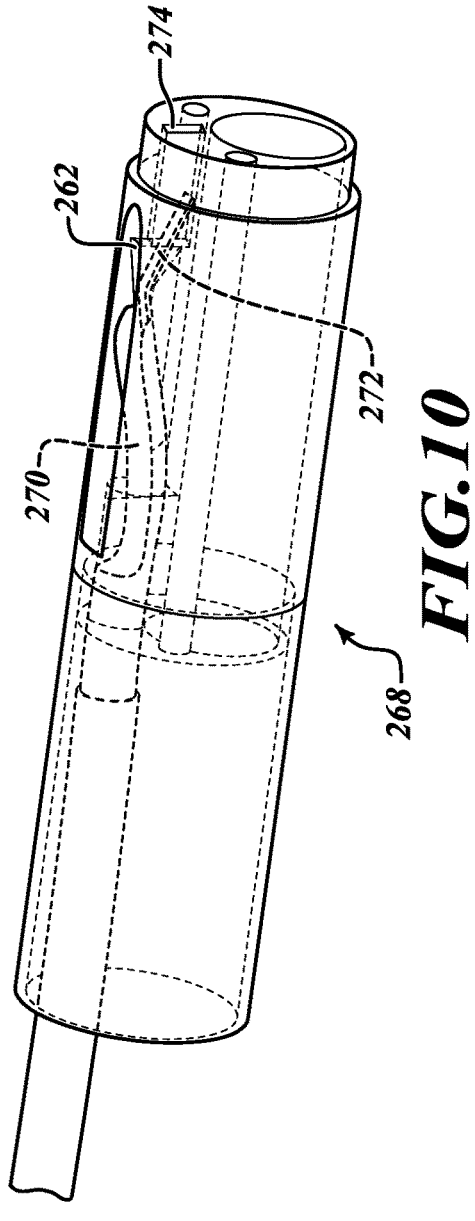
FIG. 10 is a partial x-ray isometric view of a portion of a distal end of an illustrative multi-lumen catheter.

In various embodiments, as shown in FIG. 10 a ramp section 268 of a cap section 267 of a multi-lumen catheter device includes a ramp and a plug cavity 262 for receiving a distal end of a lumen liner 270 and an associated elongated distal tab 272 extending therefrom. The ramp section 268 also includes a tab reception area 274 located distally from the plug cavity 262. The tab reception area 274 may include softer material than that used to form the cap section 267. The tab reception area 274 may also include an additional lumen or a permeable wall. The elongated distal tab 272 has a length value that is greater than a length value of the plug cavity 262. Once the lumen liner 270 has been inserted into a desired position within the ramp section 268, the elongated distal tab 272 is bent into both the plug cavity 262 and the tab reception area 274. The elongated distal tab 272 provides a locking mechanism for the lumen liner 270. After the elongated distal tab 272 has been inserted, an adhesive may be inserted into the plug cavity 262 around the tab 272.

Figure 11:
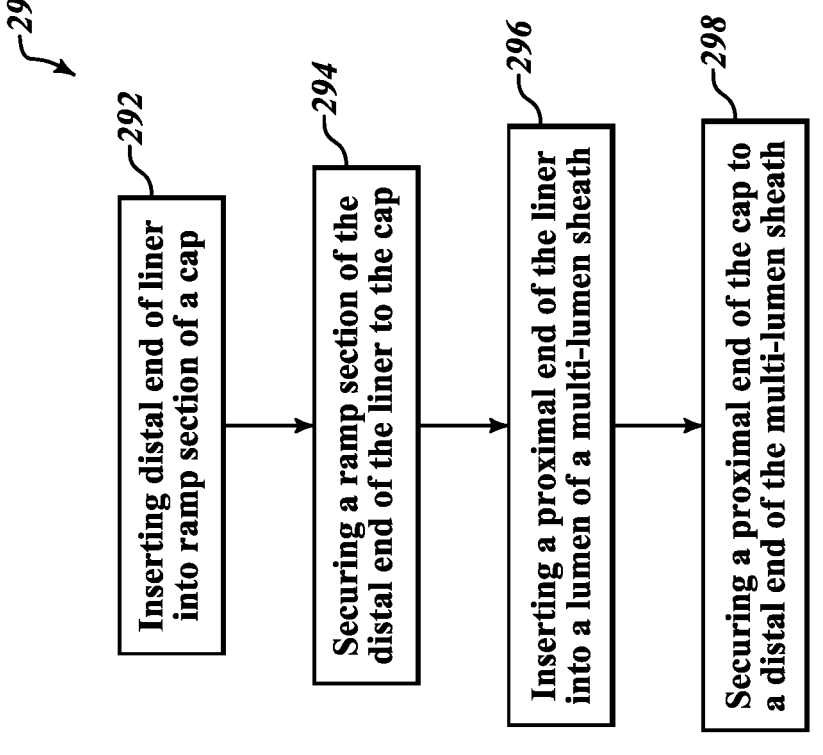
FIG. 11 is a flow diagram showing an illustrative method for creating an illustrative multi-lumen catheter.

As shown in FIG. 11, in various embodiments the method 290 shows operational steps for creating one or more of the dual-lumen catheter devices shown and described above. First at a block 292, a distal end of the lumen liner is inserted into a ramp section of the distal cap component for a dual-lumen catheter. In various embodiments, the lumen liner may need to be pre-bent prior to insertion into the ramp section. Next that a block 294, a ramp section of the distal end of the lumen liner is secured to the cap section. At a block 196, a proximal end of the lumen liner is inserted into a lumen of a multi-lumen sheath. Then at a block 198, a proximal end of the distal cap component is attached to a distal end of the multi-lumen sheath. The attachment of the distal cap component to the multi-limit sheath may be accomplished by various adhesives or by applying a heat shrink material around the components.

From the foregoing discussion and associated drawing figures, it will be appreciated that various embodiments have been disclosed and illustrated. To that end and without any implication of any limitation (which is not to be inferred), the following paragraphs set forth non-limiting summaries of various embodiments disclosed herein by way of example only and not of limitation:

A. An apparatus comprising: a multi-lumen sheath; a cap having a proximal end attachable to a distal end of the multi-lumen sheath; and a liner including: a flexible proximal section; and a distal ramp section having a C-shaped cross-section, the distal ramp section being configured to extend distally from the flexible proximal section and to be receivable by the cap.

B. The apparatus of A, wherein: the cap further including: a ramp section having a ramp and an exit port, the ramp being configured to allow travel of a medical device from within the liner to the exit port; and an imaging section disposed distally from the ramp section and being config-ured to receive an imaging device; and the distal ramp section includes a longitudinal axis having a radius of curvature along at least a portion of the distal ramp section.

C. The apparatus of B, wherein: the cap further includes a socket disposed at a distal end of the ramp; and the liner further includes a tab disposed distally from the distal ramp section, the tab being configured to be receivable within the socket.

D. The apparatus of C, wherein the liner further includes a neck section disposed between the distal ramp section and the tab.

E. The apparatus of D, wherein the tab includes a first dimension and the neck section include a second dimension, the first and second dimensions being perpendicular to the longitudinal axis of the distal ramp section, the first dimen-sion being greater than the second dimension.

F. The apparatus of A, wherein the distal ramp section further includes a bending section and a straight section.

G. The apparatus of F, wherein the bending section includes a bending relief feature.

H. The apparatus of G, wherein the bending relief feature includes a plurality of laser cuts.

I. The apparatus of C, wherein the cap further includes an adhesive receivable within the socket.

J. A system comprising: a medical device; and a multi-lumen device including: a handle including: at least two lumens; a first port in communication with a first one of the at least two lumens; and a second port being in communication with a second one of the at least two lumens, the second port and the second one of the at least two lumens being configured to slidably receive a portion of the medical device; a multi-lumen sheath attachable to the handle; a cap having a proximal end attachable to a distal end of the multi-lumen sheath; and a liner including: a flexible proximal section; and a distal ramp section having a C-shaped cross-section, the distal ramp section being configured to extend distally from the flexible proximal section and to be receivable by the cap.

K. The system of J, wherein: the cap further includes: a ramp section having a ramp and an exit port, the ramp being configured to allow travel of a medical device from within the liner to the exit port; and an imaging section disposed distally from the ramp section and being configured to receive an imaging device; and the distal ramp section includes a longitudinal axis having a radius of curvature along at least a portion of the distal ramp section.

L. The system of K, wherein: the cap includes a socket disposed at a distal end of the ramp; and the liner further includes a tab disposed distally from the distal ramp section, the tab being configured to be receivable within the socket.

M. The system of L, wherein the liner further includes a neck section disposed between the distal ramp section and the tab.

N. The system of M, wherein the tab includes a first dimension and the neck section include a second dimension, the first and second dimensions being perpendicular to the longitudinal axis of the distal ramp section, the first dimension being greater than the second dimension.

O. The system of J, wherein the distal ramp section further includes a bending section and a straight section.

P. The system of O, wherein the bending section includes a bending relief feature.

Q. The system of P, wherein the bending relief feature includes a plurality of laser cuts.

R. The system of L, wherein the cap further includes an adhesive receivable within the socket.

S. A method comprising: providing: a multi-lumen sheath; a cap having a proximal end attachable to a distal end of the multi-lumen sheath, the cap including: a ramp section having a ramp and an exit port; and an imaging section disposed distally from the ramp section; and a liner including: a flexible proximal section; and a distal ramp section having a C-shaped cross-section; inserting the distal ramp section into the cap; securing the distal ramp section within the cap; inserting a proximal end of the liner into a lumen of the multi-lumen sheath; and securing a proximal end of the cap to a distal end of the multi-lumen sheath.

T. The method of S, further comprising before inserting the distal ramp section into the cap, performing an action chosen from bending the distal ramp section and reducing a bending force of the distal ramp section.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While the disclosed subject matter has been described in terms of illustrative embodiments, it will be understood by those skilled in the art that various modifications can be made thereto without departing from the scope of the claimed subject matter as set forth in the claims.

What is claimed is:
1. An apparatus comprising:
a sheath including a lumen;
a cap having a proximal end attachable to a distal end of the sheath; and
a lumen liner at least partially secured within a distal portion of the lumen of the sheath to a distal end within the cap, the lumen liner including:
a tubular proximal section at least partially disposed within the lumen; and
a distal ramp section creating a transition from the lumen to an exit port in a sidewall of the cap, the distal ramp section including a C-shaped cross-section extending distally from the tubular proximal section and terminating in a tab, the tab receivable within a socket to secure a distal end of the distal ramp section into the cap.
2. The apparatus of claim 1, wherein:
the cap further including:
a ramp section formed in part by the distal ramp section of the lumen liner, the ramp section having a ramp and an exit port, the ramp being configured to allow travel of a medical device from within the liner to the exit port; and
an imaging section disposed distally from the ramp section and being configured to receive an imaging device; and
the distal ramp section includes a longitudinal axis having a radius of curvature along at least a portion of the distal ramp section.
3. The apparatus of claim 2, wherein:
an opening in the liner formed by the C-shaped cross-section of the distal ramp section forms the exit port.
4. The apparatus of claim 2, wherein the liner further includes a neck section disposed between the distal ramp section and the tab.
5. The apparatus of claim 4, wherein the tab includes a first dimension and the neck section include a second dimension, the first and second dimensions being perpendicular to the longitudinal axis of the distal ramp section, the first dimension being greater than the second dimension.
6. The apparatus of claim 1, wherein the distal ramp section further includes a bending section and a straight section.
7. The apparatus of claim 6, wherein the bending section includes a bending relief feature.
8. The apparatus of claim 7, wherein the bending relief feature includes a plurality of laser cuts.
9. The apparatus of claim 3, wherein the cap further includes an adhesive receivable within the socket.
10. A system comprising:
a medical device;
an imaging device; and
a multi-lumen device including:
a handle including:
at least two lumens;
a first port in communication with a first lumen of the at least two lumens; and
a second port being in communication with a second lumen one of the at least two lumens, the second port and the second one of the at least two lumens being configured to slidably receive a portion of the medical device;
a multi-lumen sheath attachable to the handle;

10 a cap having a proximal end attachable to a distal end of the multi-lumen sheath; and
a liner at least partially secured within a distal portion of the second lumen, the liner including:
a tubular proximal section disposed at least partially within the second lumen; and
a distal ramp section extending distally from the tubular proximal section, the distal ramp section including a C-shaped cross-section extending distally from the tubular proximal section and terminating in a tab, the tab receivable within a socket to secure a distal end of the distal ramp section into the cap,
wherein the cap includes a distal cap section to receive the imaging device to image the medical device upon extension out of the distal ramp section.
11. The system of claim 10, wherein:
the cap further includes:
a ramp section having a ramp and an exit port, the ramp being configured to allow travel of the medical device from within the liner to the exit port; and
an imaging section disposed distally from the ramp section and being configured to receive the imaging device; and
the distal ramp section includes a longitudinal axis having a radius of curvature along at least a portion of the distal ramp section.
12. The system of claim 11, wherein:
an opening in the liner formed by the C-shaped cross-section of the distal ramp section forms the exit port.
13. The system of claim 11, wherein the liner further includes a neck section disposed between the distal ramp section and the tab.
14. The system of claim 13, wherein the tab includes a first dimension and the neck section include a second dimension, the first and second dimensions being perpendicular to the longitudinal axis of the distal ramp section, the first dimension being greater than the second dimension.
15. The system of claim 10, wherein the distal ramp section further includes a bending section and a straight section.
16. The system of claim 15, wherein the bending section includes a bending relief feature.
17. The system of claim 16, wherein the bending relief feature includes a plurality of laser cuts.
18. The system of claim 12, wherein the cap further includes an adhesive receivable within the socket.
19. A method comprising:
providing:
a multi-lumen sheath;
a cap having a proximal end attachable to a distal end of the multi-lumen sheath, the cap including:
a ramp section having a ramp and an exit port; and
an imaging section disposed distally from the ramp section; and
a liner including:
a tubular proximal section; and
a distal ramp section including a C-shaped cross-section extending distally from the tubular proximal section and terminating in a tab;
inserting the distal ramp section into the cap;
securing the distal ramp section within the cap including inserting the tab into a socket in the cap;
applying a medical grade adhesive into the socket to secure the tab;
inserting a proximal end of the liner into a lumen of the multi-lumen sheath; and securing a proximal end of the cap to a distal end of the
multi-lumen sheath.

20. The method of claim 19, further comprising before
inserting the distal ramp section into the cap, performing an
action chosen from bending the distal ramp section and
reducing a bending force of the distal ramp section.

* * * * *